United States Patent [19]

Nishimura et al.

[11] Patent Number: 4,876,382
[45] Date of Patent: Oct. 24, 1989

[54] PROCESS FOR MAKING FLUOROBENZOIC ACID FLUOROPHENYLESTERS

[75] Inventors: Yasunobu Nishimura, Kamifukuoka; Toshikazu Kawai, Kawagoe, both of Japan

[73] Assignee: Central Glass Company, Limited, Ube, Japan

[21] Appl. No.: 143,636

[22] Filed: Jan. 13, 1988

[30] Foreign Application Priority Data

Jan. 30, 1987 [JP] Japan .................................. 62-18507
Jan. 30, 1987 [JP] Japan .................................. 62-18508

[51] Int. Cl.$^4$ ............................................ C07C 69/76
[52] U.S. Cl. ...................................... 560/109; 568/332
[58] Field of Search ......................................... 560/109

[56] References Cited

U.S. PATENT DOCUMENTS 4,393,231 7/1983 Masaki .............................. 560/109

FOREIGN PATENT DOCUMENTS 3526235 5/1986 Fed. Rep. of Germany .
61-87646 5/1986 Japan .
WO/02067 10/1986 PCT Int'l Appl. .

OTHER PUBLICATIONS

CA 93 (25):231919t, 1980.
"The Peracetic Acid Clevage of Unsymmetrical Ketones", by W. von E. Doering et al., J. Am. Chem. Soc., vol. 72, 1950, pp. 5515–5518.
"Reactions of Peracids. V.[1] The Reaction of Substituted Acetophenones with Perbenzoic Acid[2]", by S. L. Friess et al., J. Am. Chem. Soc., vol. 73, (1951), pp. 3968–3972.

Primary Examiner—Paul J. Killos
Attorney, Agent, or Firm—Fleit, Jacobson, Cohn, Price, Holman & Stern

[57] ABSTRACT

Two kinds of novel fluorobenzophenones represented by the general formula (A), wherein X is F or Cl, are synthesized from 1,2-difluorobenzene and 4,4'-difluorobenzophenone, respectively. Novel fluorophenyl fluorobenzoates represented by the general formula (B), wherein X is F or Cl, are obtained by oxidizing the fluorobenzophenones (A), respectively, in an organic solvent by using trifluoroacetic acid and aqueous solution of hydrogen peroxide. By hydrolysis of each of the fluorobenzoates (B), 3,4-difluorophenol or 3-chloro-4-fluorophenol can easily be obtained.

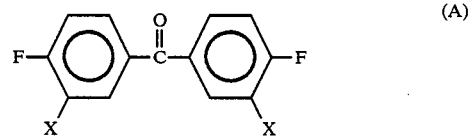

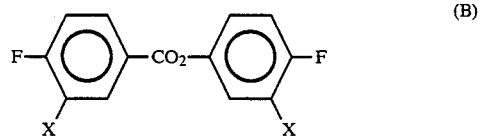

4 Claims, No Drawings

PROCESS FOR MAKING FLUOROBENZOIC ACID FLUOROPHENYLESTERS

BACKGROUND OF THE INVENTION

This invention relates to a group of novel fluorobenzophenones having two fluorine or chlorine atoms additional to the structure of 4,4'-difluorobenzophenone and conversion of the novel fluorobenzophenones into corresponding fluorobenzoic acid fluorophenylesters which too are novel compounds. The novel compounds will be useful in preparing medicines, agricultural chemicals and other functional materials.

4,4'-Difluorobenzophenone is a well known compound which is of use as a material of heat resistant polymers. However, further fluorination or chlorination of this compound has not been reported. As to fluorinated benzoic acid phenylesters, JP-A 61-87646 shows exclusively ones having an asymmetric structure.

SUMMARY OF THE INVENTION

It is an object of the present invention to provide novel fluorobenzophenones which have fluorine or chlorine substituents additional to the structure of 4,4'-difluorobenzoic acid.

It is another object of the invention to provide novel fluorobenzoic acid fluorophenylesters as derivatives of the novel fluorobenzophenones.

It is a further object of the invention to provide a preparation method for each of the novel fluorobenzophenones.

It is a still further object of the invention to provide a method for preparing the novel fluorobenzoic acid fluorophenylesters from the novel fluorobenzophenones.

Generically, the present invention provides halogenated diphenyl compounds reresented by the general formula (1).

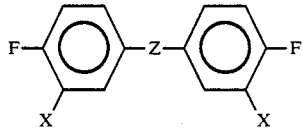

wherein Z represents

or $-CO_2-$, and X represents F or Cl.

That is, novel compounds of the invention are two kinds of fluorobenzophenones represented by the general formula (2), wherein X is as defined above, and two kinds of fluorobenzoic acid fluorophenylesters represented by the general formula (3), wherein X is as defined above.

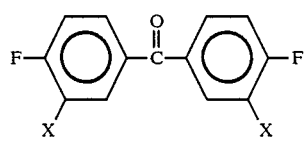

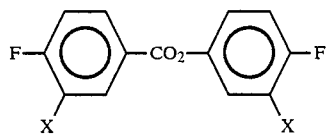

In the compounds of the general formula (2), 3,3'-4,4'-tetrafluorobenzophenone is a colorless liquid having a boiling point of 144°–146° C. at 10 mmHg. According to the invention this compound is prepared by first reacting 1,2-difluorobenzene with carbon tetrachloride in the presence of anhydrous aluminum chloride and then hydrolyzing the reaction product in an acidic solution containing sulfuric acid. This method will be favorable for industrial application, though it is also possible to obtain the same compound by subjecting 3,4-difluorobenzoic acid chloride and 1,2-difluorobenzene to a ketone forming reaction in the presence of a Lewis acid such as aluminum chloride.

Another compound of the general formula (2) is 3,3'-dichloro-4,4'-difluorobenzophenone, which is in the form of colorless platy crystals having a melting point of 91-93.5° C. According to the invention this compound is Prepared by reacting 4,4'-difluorobenzophenone with chlorine gas in the presence of anhydrous aluminum chloride. This method will be favorable for industrial application, though it is also possible to obtain the same compound by the steps of subjecting 3-chloror-4-trifluorobenzoic acid chloride and fluorobenzene to a ketone forming reaction in the presence of a Lewis acid such as aluminum chloride to thereby obtain 3-chloro-4,4'-difluorobenzophenone and chlorinating it.

One of the compounds represented by the general formula (3) is 3',4'-difluorophenyl-3,4-difluorobenzoate. This compound is in the form of colorless needle-like crystals having a melting point of 80–82° C. The other compound is 3'-chloro-4'-fluorophenyl-3-chloro-4-fluorobenzoate, which is in the form of colorless needle-like crystals having a melting point of 97°–99° C. Either of these two compounds is obtained by oxidizing 3,3', 4,4'tetrafluorobenzophenone or 3,3'-dichloro-4,4'-difluorobenzophenone by using hydrogen peroxide and trifluoroacetic acid in the presence of a suitable organic solvent.

As an important merit of the present invention, each fluorophenyl fluorobenzoate of the general formula (3) can easily be hydrolyzed into a fluorophenol and a fluorobenzoic acid. That is, by utilizing this invention it is easy to obtain either 3,4-difluorophenol which is useful as an intermediate material of, for example, herbicides or liquid crystals or 3-chloror-4-fluorophenol which is useful as an intermediate material of, for example, insecticides. The by-produced fluorobenzoic acid can be used as an intermediate material of some medicines and agricultural chemicals, or may alternatively be converted into a fluorobenzoic acid chloride from which a fluorobenzophenone of the general formula (1) can be synthesized as mentioned hereinbefore.

DETAILED DESCRIPTION OF THE INVENTION

The novel fluorobenzophenones of the general formula (2) can easily be prepared by the methods described hereinbefore.

Each of the novel fluorophenyl fluorobenzoates of the general formula (3) is obtained by oxidizing a corresponding fluorobenzophenone of the general formula (2) in an organis solvent by using trifluoroacetic acid and hydrogen peroxide. The mechanism of this oxidation is considered to be analogous to usual Baeyer-Villiger reactions using an organic peracid.

Representatives of organic peracids are perbenzoic acid, m-chloroperbenzoic acid, peracetic acid and trifluoroperacetic acid. However, when a benzophenone compound or an acetophenone compound is subjected to Baeyer-Villiger reaction using a peracid other than trifluoroperacetic acid the rate of reaction is too low for industrial application: usually it takes 8 to 30 days to complete the reaction (J. Am. Chem. Soc., 72, 5515 (1950) and J. Am. Chem. Soc., 73. 3968 (1951) ). Trifluoroperacetic acid is obtained by reacting anhydrous trifluoroacetic acid with concentrated hydrogen peroxide. However, anhydrous trifluoroacetic acid is an expensive material, and concentrated hydrogen peroxide is a dangerous material not easy to industrially acquire and handle.

In the present invention the Baeyer-Villiger reaction of a novel fluorobenzophenone is accomplished by using a mere mixture of trifluoroacetic acid and an aqueous solution of hydrogen peroxide without preparing trifluoroperacetic acid in advance. In this case it is presumed that the oxidizing reaction proceeds by joint action of trifluoroacetic acid and hydrogen peroxide on the fluorobenzophenone while trifluoroperacetic acid is not substantially formed. The presumption is supported by the fact that, in contrast to usual Baeyer-Villiger reactions using trifluoroperacetic acid with addition of a salt such as sodium hydrogenphosphate or sodium hydrogencarbonate in order that the reaction liquid may not become strongly acidic, the addition of such a salt to the reaction system according to the invention causes the oxidizing reaction to stop proceeding as a consequence of almost complete neutralization of trifluoroacetic acid.

In the oxidizing reaction at least 1 mol, and preferably at least 2 mols, of trifluoroacetic acid is used per mol of the fluorobenzophenone to be oxidized.

The oxidizing reaction is carried out in an organic solvent that is stable under the oxidizing conditions. It is possible to use trifluoroacetic acid also as the solvent by charging it in large excess of necessity for the reaction. Otherwise, it is suitable to use a halogenated hydrocarbon such as dichloromethane, carbon tetrachloride, 1,2-dichloroethane or 1,1,2,2-tetrachloroethane. The quantity of the organic solvent is not specified. In the case of using a nonpolar solvent the quantity of the solvent is desired to be such that the addition of an aqueous hydrogen peroxide solution to the fluorobenzophenone solution provides a homogeneously mixed solution without separating into two layers.

The concentration of the aqueous solution of hydrogen peroxide is not particularly limited. For instance, the concentration may be as low as about 3% or may be close to 100%. In practice it is favorable to use a 25-40% aqueous solution of hydrogen peroxide because of ease of handling and industrial purchasing.

The oxidizing reaction is an exothermic reaction. To suppress self-decomposition of the oxidized product it is preferred to carry out the reaction at a temperature not higher than 50° C.

The product of the oxidizing reaction is 3′, 4′-difluorophenyl-3,4-difluorobenzoate or 3′-chloro-4′-fluoro-3-chloro-4-fluorobenzoate. Either 3,4-difluorophenol or 3-chloro-4-fluorophenol can easily be obtained by hydrolyzing the fluorobenzoate, which does not need to be refined in advance. The hydrolysis can be accomplished by a known method for hydrolyzing esters, and the fluorophenol is obtained at nearly 100% yield. Besides, 3,4-difluorobenzoic acid or 3-chloro-4-fluorobenzoic acid is formed by the hydrolysis treatment. This by-product may be used in synthesizing medicines or agricultural chemicals or may alternatively be used for synthesizing (e.g. by using thionyl chloride as a reagent) a difluorobenzoic acid chloride or a chlorofluorobenzoic acid chloride from which a fluorobenzophenone of the general formula (2) can be prepared.

From an industrial point of view, the preparation of fluorophenols from the novel fluorobenzoates of the general formula (3) is advantageous over known methods which involve some problems as outlined below.

In the case of preparing a fluorophenol from a fluoroaniline by Sandmeyer reaction a large quantity of sulfuric acid or an alternative acid must be used and, besides, the starting material is not readily available. In the case of subjecting an aminophenol to Schiemann reaction it is necessary to use high-purity borofluoric acid, which is expensive and cannot be reused. Hydrolysis of a bromofluorobenzene must be carried out under severe reaction conditions and is often accompanied by defluorinating reaction which gives unsubstituted phenol difficult to separate from the fluorophenol. Acid decomposition of a fluoroanisole suffers from relatively high price of the starting material and difficulty of obtaining fluoroanisoles except 4-fluoroanisole. Oxidation of a fluorobenzoic acid is not convenient for industrial practice.

The invention is further illustrated by the following nonlimitative examples.

EXAMPLE 1

This example relates to preparation of 3,3′, 4,4′-tetrafluorobenzophenone as represented by the following reaction formula.

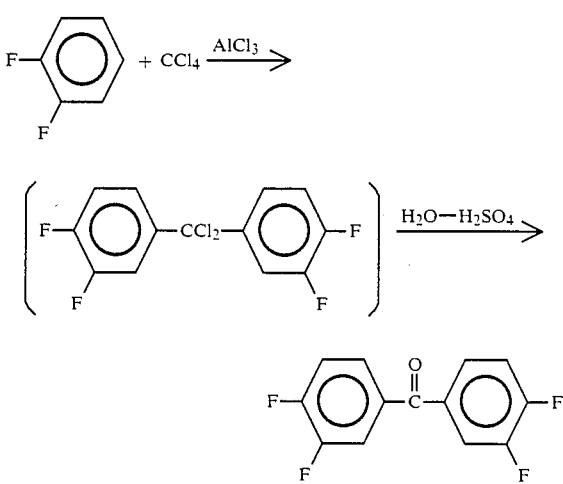

In a 200 ml three-necked flask provided with thermometer, dropping funnel and reflux condenser, 22.8 g (0.20 mol) of 1,2-difluorobenzene and 15 g (0.11 mol) of anhydrous aluminum chloride were kept cooled at 12° by using a bath, and 61.5 g (0.4 mol) of carbon tetrachloride was dropped by the dropping funnel in 1.5 hr. After that the temperature in the flask was raised to 30° and stirring was continued for 3.5 hr while hydrogen chloride formed by the reaction was dissipated from the reaction system at the top of the reflux condenser.

After the above reaction the mixture in the flask was transferred into iced water, and organic matter was extracted with dichloromethane. Then dichloromethane, carbon tetrachloride and unreacted 1,2-difluorobenzene were removed from the extract to thereby obtain 25 g of an intermediate compound in the form of Yellow oil.

The intermediate compound was put into a 100 ml egg-type flask connected with a reflux condenser, and 10 g of water and 10 g of 98% sulfuric acid were added. The resultant mixture was heated for 9.5 hr at reflux temperature. After cooling the reaction liquid 60 ml of water was added, and organic matter was extracted with ether. The extract was washed first with 5% sodium carbonate solution and then with water and was dried with magnesium sulfate. After completely removing ether the organic matter was subjected to distillation under reduced pressure to obtain 17.4 g (Yield 67%) of 3,3',4,4'-tetrafluorobenzophenone of 98.1% purity having a boiling point of 44°–146° C. at 10 mmHg. Analysis of this compound gave the following data.

$^{19}$F-NMR (in CDCl$_3$; standard: CF$_3$COOH): δ+46.5 ppm (m), +51.7 ppm (m).

MS (mass spectrograph) m/z (%): 254 (M$^{30}$, 45), 113 (29), 141 (100), 255(7).

IR absorption (KBr pellet): 1670 cm$^{-1}$.

EXAMPLE 2

This example relates to the preparation of 3,3'-dichloro-4,4'-difluorobenzophenone as represented by the following reaction formula.

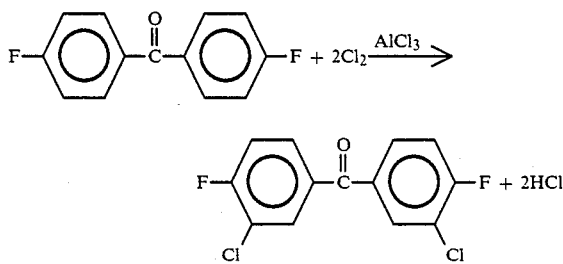

In a cylindrical glass reactor connected with a chloring gas introducing pipe, 5 g (0.023 mol) of 4,4'-difluorobenzophenone was charged together with 6.1 g (0.046 mol) of anhydrous aluminum chloride and 25 ml of carbon tetrachloride. The mixture was kept heated at 50° C., and chloring gas was blown into the reactor for 3.5 hr at a rate of 0.014 mol/hr.

After the above chlorinating reaction the mixture in the reactor was transferred into iced water, and organic matter was extracted with carbon tetrachloride. The extract was washed first with 5% sodium carbonate solution and then with water, followed by drying with magnesium sulfate, and the remaining solvent was completely removed to thereby obtain 5.8 g of a colorless solid product. By gas chromatography this solid product contained 7.6% of monochloro-derivative, 84.4% of dichloro-derivative and 4.5% of trichloroderivative. The crude solid product was twice recrystallized from methanol to thereby obtain 3.9 g (Yield 59.!%) of colorless platy crystals of 3,3'-dichloro-4,4'-difluorobenzophenone of 98.8% purity. The melting point of this product was 91°–93.5° C. Analysis of the obtained compound gave the following data.

$^{19}$F-NMR (in CDCl$_3$; standard: CF$_3$COOH): δ+26.0 ppm (m).

MS m/z (%): 286 (M+, 43), 129 (18), 157 (100), 288 (27), 290 (4).

IR absorption (KBr): 1662 cm $^{-1}$.

EXAMPLE 3

In a glass reactor 3 g of 3,3', 4,4'-tetrafluorobenzophenone was dissolved in 30 g of trifluoroacetic acid, and, while stirring, 2 g of 30% aqueous solution of hydrogen peroxide was added. At room temperature the mixed solution was stirred for 24 hr to carry out oxidation reaction. After that water was added to the reaction liquid to transfer trifluoroacetic acid into an aqueous layer, and then organic matter was extracted with dichloromethane. The extract was washed first with 5% sodium carbonate solution and then with water and was dried with magnesium sulfate. As the result 3', 4'-difluorophenyl-3,4-difluorobenzoate was obtained at 91.9% Yield. BY the oxidation reaction the conversion of the starting fluorobenzophenone was 97.7%. Using methanol the product was recrystallized to obtain colorless needle-like crystals having a melting point of 80°–82° C. Analysis of the obtained fluorobenzoate gave the following data.

$^{19}$F-NMR (in CDCl$_3$; standard: CF$_3$COOH): δ30 45.0 ppm (m), +50.3 ppm (m), +51.6 ppm (m), +56.0 ppm (m). MS m/z (%): 270 (M+, 4), 113 (25), 141 (100).

IR absorption (KBr): 1750 cm$^{-1}$.

The fluorobenzoate was put into a solution of sodium hydroxide in methanol, and the mixture was stirred and heated for 1 hr at reflux temperature. After cooling methanol was removed, and the reaction liquid was rendered acidic by addition of hydrochloric acid. Then the liquid was rendered alkaline by addition of 5% solution of sodium carbonate to thereby liberate 3,4-fluorophenol, which was extracted with ether. The remaining aqueous layer was again rendered acidic by addition of hydrochloric acid to cause precipitation of a white solid. The precipitate was dissolved in and extracted with ether, and the extract was dried and concentrated to thereby obtain 3,4-difluorobenzoic acid.

EXAMPLE 4

Oxidation of 3,3'-dichloro-4,4'-difluorobenzophenone was accomplished by the same method as in Example 3. In this case the conversion of the starting benzophenone was 85.9%, and 3'-chloro-4'-fluorophenyl-3-chloro-4-fluorobenzoate was obtained at 82.4% yield. After recrystallization, the product was in the form of colorless needle-like crystals having a melting point of 97°–99° C. Analysis of the obtained benzoate gave the following data.

$^{19}$F-NMR (in CDCl$_3$; standard: CF$_3$COOH): δ+24.4 ppm (m), +35.7 ppm (m).

MS m/z (%): 302 (M+, 6), 129 (41), 157 (100), 304 (4).

IR absorption (KBr): 1750 cm $^{-1}$.

BY hydrolyzing the obtained benzoate by the method described in Example 3, 3-chloro-4-fluorophenol was obtained together with 3-chloro-4-fluorobenzoic acid.

What is claimed is:

1. A method of preparing a fluorophenyl fluorbenzoate represented by the formula (3),

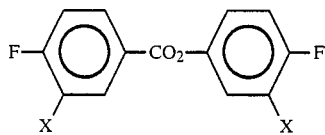

wherein X is F or Cl, comprising oxidizing a fluorobenzophenone represented by the formula (2) in an organic solvent by using trifluoroacetic acid and hydrogen peroxide,

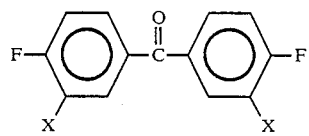

wherein X is F or Cl;

wherein at least 1 mol of trifluoroacetic acid is used per mole of the fluorobenzophenone to be oxidized; and wherein the oxidation of the fluorobenzophenone is carried out at a temperature not higher than 50° C.

2. A method according to claim 1, wherein said organic solvent is trifluoroacetic acid.

3. A method according to claim 1, wherein said organic solvent is a halogenated hydrocarbon selected from the group consisting of dichloromethane, carbon tetrachloride, 1,2-dichloroethane and 1,1,2,2-tetraohioroethane.

4. A method according to claim 1, wherein said hydrogen peroxide is in the form of 25-40% solution in water.

* * * * *